United States Patent
Zoumalan

(10) Patent No.: US 11,213,473 B1
(45) Date of Patent: Jan. 4, 2022

(54) SKIN BRIGHTENING COMPOSITION

(71) Applicant: Christopher Zoumalan, Los Angeles, CA (US)

(72) Inventor: Christopher Zoumalan, Los Angeles, CA (US)

(*) Notice: Subject to any disclaimer, the term of this patent is extended or adjusted under 35 U.S.C. 154(b) by 0 days.

(21) Appl. No.: 17/024,911

(22) Filed: Sep. 18, 2020

(51) Int. Cl.
| | |
|---|---|
| *A61K 8/67* | (2006.01) |
| *A61K 8/49* | (2006.01) |
| *A61K 8/60* | (2006.01) |
| *A61K 8/64* | (2006.01) |
| *A61K 8/06* | (2006.01) |
| *A61Q 19/08* | (2006.01) |
| *A61K 8/44* | (2006.01) |
| *A61K 8/29* | (2006.01) |
| *A61Q 19/02* | (2006.01) |

(52) U.S. Cl.
CPC .............. *A61K 8/678* (2013.01); *A61K 8/062* (2013.01); *A61K 8/29* (2013.01); *A61K 8/44* (2013.01); *A61K 8/4926* (2013.01); *A61K 8/602* (2013.01); *A61K 8/64* (2013.01); *A61K 8/676* (2013.01); *A61Q 19/02* (2013.01); *A61Q 19/08* (2013.01); *A61K 2800/43* (2013.01); *A61K 2800/805* (2013.01)

(58) Field of Classification Search
None
See application file for complete search history.

(56) References Cited

U.S. PATENT DOCUMENTS

| | | |
|---|---|---|
| 5,741,509 A | 4/1998 | Kushner |
| 7,241,451 B1 | 7/2007 | Edell et al. |
| 8,021,683 B2 | 9/2011 | Berlat |
| 8,263,114 B2 | 9/2012 | Berlat |
| 10,496,949 B2 | 12/2019 | Zoumalan |
| 2008/0317822 A1 | 12/2008 | Azimi |
| 2009/0143333 A1 | 6/2009 | Palefsky et al. |
| 2010/0062085 A1 | 3/2010 | Widgerow |
| 2015/0342853 A1* | 12/2015 | Santhanam ............. A61K 8/66 424/62 |
| 2016/0206540 A1* | 7/2016 | Hood .................. A61K 8/4946 |
| 2018/0298067 A1* | 10/2018 | Walther ............... C07K 14/461 |

\* cited by examiner

*Primary Examiner* — David J Blanchard
*Assistant Examiner* — Sarah J Chickos
(74) *Attorney, Agent, or Firm* — Eandi Fitzpatrick LLP

(57) ABSTRACT

A composition to improve hyperpigmentation is disclosed. The composition has one or more active ingredients such as tranexamic acid, niacinamide, arbutin, and Vitamin C. The composition has water, caprylic/capric triglyceride, C12-15 Alkyl Benzoate, Isononyl Isononanoate, Silica, Glyceryl Stearate and PEG-100 Stearate, Cetearyl Alcohol and Ceteareth-20, Xylitylglucoside and Anhydroxylitol and Xylitol, Hydroxyethyl Acrylate/Sodium Acryloyldimethyl Taurate Copolymer, Polysorbate 60, Phenoxyethanol and Ethylhexylglycerin, Citric Acid, Titanium Dioxide, Citrus oil, sh-Polypeptide-22, and sh-Oligopeptide-1. The composition is a non-HQ formulation that provides equal or greater efficacy with a reduced adverse reaction profile to improve skin hyperpigmentation, such as melasma, post-inflammatory hyperpigmentation, and solar lentigines. The composition reduces skin damage and provides toning to the skin.

2 Claims, 5 Drawing Sheets

SKIN BRIGHTENING COMPOSITION

FIELD OF THE INVENTION

The present invention generally relates to medical and cosmetic compositions. More specifically, the present invention relates to a medical and cosmetic composition for use in skin brightening and treating hyperpigmentation, and to a method of preparing the composition.

BACKGROUND

Hyperpigmentation is a common concern of patients in aesthetic practice. It could result from conditions such as melasma, post-inflammatory hyperpigmentation (PIH), and solar lentigines. Skin tone evenness and/or the appearance of hyperpigmentary spots, such as solar lentigines (age spots), are common concerns among beauty-conscious consumers. As such, cosmetic compositions and methods for addressing these consumer concerns are continuing areas of high interest.

There are various treatment options available for hyperpigmentation, but the first-line treatment includes topical depigmenting agents such as hydroquinone (HQ 2.0-4.0%). It may also include the use of tretinoin, azelaic acid, superficial peeling agents, and/or lasers. In melanocytes, the ubiquitin-proteasome system is known to regulate skin pigmentation by degrading tyrosinase or microphthalmia-associated transcription factor.

Despite many possible treatment options, the results with these treatments are often temporary, especially in melasma, as the discoloration generally returns with continued exposure to the sun. Hydroquinone (HQ) is the most widely used and studied among possible treatment options. HQ's ability to lighten hyperpigmentation stems from its competitive inhibition of the enzyme tyrosinase, which prevents the conversion of tyrosine to dopamine, ultimately halting melanin synthesis. Although effective and dosed at different strengths, HQ causes an irritant dermatitis in some individuals, and chronic use could lead to exogenous ochronosis. Its use has been historically controversial due to some animal studies that have shown toxicity to DNA, renal, and liver cells. Besides, prior animal studies state that its long-term use causes side effects and potential controversy. Due to such concerns, the use of HQ as a cosmetic additive has been banned in the European Union, and only available as a prescription.

In light of the above-mentioned problems, there is a consumer demand for non-HQ topical formulations that provide similar or better efficacy, but with a reduced adverse reaction profile to HQ. Also, there is a need for a medicinal and cosmetic composition having for skin brightening to improve hyperpigmentation.

SUMMARY OF THE INVENTION

The present invention generally discloses medical and cosmetic compositions. Further, the present invention discloses a medical and cosmetic composition for use in skin brightening to improve hyperpigmentation and a method of preparing the composition.

In one embodiment, the composition comprises one or more active ingredients including tranexamic acid, niacinamide, arbutin, and Vitamin C. The composition comprises the active ingredients in the range from about 1.0% to about 6.0% by weight. In one embodiment, the composition comprises the tranexamic acid in the range from about 1.0% to about 5.0% by weight. In one embodiment, the composition comprises the niacinamide in the range of about 3.0% to about 5.0% by weight. In one embodiment, the composition comprises arbutin in the range of about 1.0% to 3.0% by weight. In one embodiment, the composition comprises the Vitamin C in the range from about 2.0% to about 5.0% by weight. In one embodiment, Vitamin C is Tetrahexyldecyl Ascorbate. In one embodiment, the Tetrahexyldecyl Ascorbate is oil soluble, and in other embodiments, it may be water-soluble.

The composition further comprises water, caprylic/capric triglyceride, C12-15 Alkyl Benzoate, Isononyl Isononanoate, Silica, Glyceryl Stearate and PEG-100 Stearate, Cetearyl Alcohol and Ceteareth-20, Xylitylglucoside and Anhydroxylitol and Xylitol, Hydroxyethyl Acrylate/Sodium Acryloyldimethyl Taurate Copolymer, Polysorbate 60, Phenoxyethanol and Ethylhexylglycerin, Citric Acid, Titanium Dioxide, Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil, Sh-Polypeptide-22, and Sh-Oligopeptide-1.

In one embodiment, a method of preparing the composition comprises the following steps: At one step, phase-A is prepared by dissolving Titanium dioxide into water under moderate mixing. At another step, Hydroxyethyl Acrylate/Sodium Acryloyldimethyl Taurate Copolymer is added to phase-A and the mixture is heated until fully hydrated. In one embodiment, the mixture is heated to about 80° C. At another step, phase-B is prepared by heating and mixing one or more ingredients including Caprylic/Capric Triglyceride, Isononyl Isononanoate, C12-15 Alkyl Benzoate, Glyceryl Stearate and PEG-100 Stearate, Cetearyl Alcohol and Ceteareth-20, Tetrahexyldecyl Ascorbate, and Polysorbate 60. The ingredients are weighed and heated in a separate container. In one embodiment, the mixture is heated to about 80° C. with moderate mixing.

At another step, a main phase is prepared by adding phase-B to phase-A. In one embodiment, phase-B is slowly added to phase-A at about 80° C. and continuously mixed for about 5 minutes. Then the heat is turned off. At another step, one or more ingredients such as Phenoxyethanol and Ethylhexylglycerin, Tranexamic Acid, Niacinamide, and Arbutin are added to the main phase. The ingredients are continuously mixed until all solids dissolved. At another step, silica is added to the mixer obtained from the previous step. At another step, further ingredients such as Xylitylglucoside and Anhydroxylitol and Xylitol, Sh-Oligopeptide-1, Sh-Polypeptide-22, and Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil are added to the mixer obtained at step previous step and mixing until obtaining homogeneous. In one embodiment, the further ingredients are added to the mixer of the previous step at about 40° C. and mixed continuously until homogeneous.

In one embodiment, the composition comprises two synthetic growth factors comprising epidermal growth factor (EGF) and transforming growth factor-B1 (TGF-Beta 1). In one embodiment, the composition comprises EGF of about 10 ug/ml. In one embodiment, the composition comprises the TGF-Beta 1 in the range from about 10 ug/ml to about 20 ug/ml. In one embodiment, the composition has a pH of about 6.38 (as is at 25° C.). In one embodiment, the composition has a viscosity of about 183,000 cps (at 25° C., RVT spindle 63, and 5 rpm). In one embodiment, the composition is a serum, a lotion, a cream, a hydrogel, a mask, a stick, or a patch. In one embodiment, the composition is applied to an area of skin of the face, neck, hands having signs of aging, or on an area presenting wrinkles or skin lines. The composition is a non-HQ formulation that provides equal or greater efficacy with a reduced adverse reaction profile to improve skin hyperpigmentation, such as melasma, post-inflammatory hyperpigmentation, and solar lentigines. The composition reduces skin damage and provides toning to the skin.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

Figure 1:
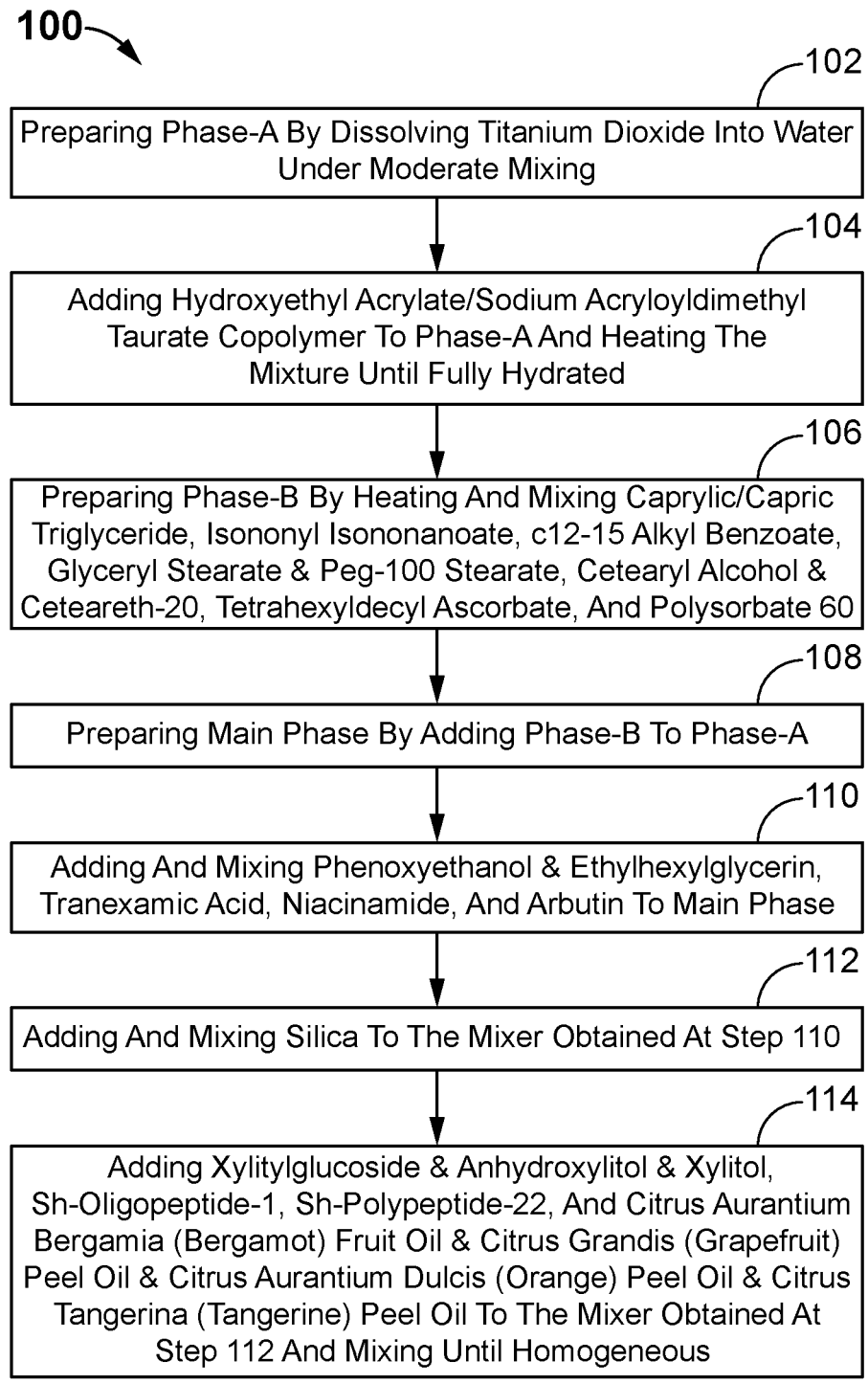
FIG. 1 shows a flowchart of a method for preparing the composition according to an an embodiment of the present invention.

The present invention is best understood by reference to the detailed figures and description set forth herein.

It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices and materials are described, although any methods, techniques, devices, or materials similar or equivalent to those described herein may be used in the practice or testing of the present invention.

Definitions

"Composition" references to that specific composition contemplated in the Summary of the Invention that can be used to rejuvenate skin that has been damaged by scarring or which has simply been affected over the years by intrinsic aging, burns and scarring.

"Derivatives" as used herein refers to structurally similar compounds that exhibit a common activity (e.g., antioxidant) and contain at least one significant, common structural element with the compound from which it is derived, which common structural element provides the common activity.

"Growth factors" as used herein refers to plant growth factors such as kinetin, a plant-based growth factor that functions mainly to protect the skin from free radical damage. "Growth factors" may also refer to human or synthetic growth factors. Synthetic growth factors may be developed to be approximately identical to growth factors found in human skin, designed to enhance epidermal growth and keratinization, and may comprise, for example, transforming growth factor (TGF) Beta 1, 2, 3, Interleukin-6 (IL-6) and Vascular endothelial growth factor (VEGF), and Epidermal Growth Factor (EGF).

HQ4% as used herein refers to formulas with 4.0% Hydroquinone.

"Pharmaceutically-acceptable topical carrier" and equivalent terms refer to an inactive liquid or cream vehicle capable of suspending or dissolving the aromatic aldehyde and having the properties of being nontoxic and non-inflammatory when applied to the skin. Representative carriers include water, oils, both vegetable and mineral, cream bases, lotion bases, ointment bases and the like. These bases include suspending agents, thickeners, penetration enhancers and the like. Their formulation is well known to those in the art of cosmetics and topical pharmaceuticals.

"Therapeutically effective dose" is defined as a dose of a composition of this invention which, when applied topically to the skin of a patient afflicted with a dermatologic or other cosmetic or medical condition, or when administered by another route, results in an observable improvement in the patient's condition.

"Topical" refers to a mode of administration and means that a material is administered by being applied to the skin.

"Topically effective" means that a material, when applied to the skin, produces a desired pharmacological result either locally at the place of application or systemically as a result of transdermal passage of an active ingredient in the material.

Now, with reference to the composition for improving the appearance of skin, and in particular, brightening skin and improving hyperpigmentation, the composition of the present invention is, in some embodiments, applied topically, and may be a cream, gel, ointment, lotion, paste, jelly mask or other topical.

With reference to FIG. 1, a flowchart of an exemplary method 100 for preparing the composition, according to one embodiment of the present invention. The composition is prepared using one or more active ingredients and other ingredients listed in a table as shown in Table 1. In one embodiment, the composition comprises one or more active ingredients including tranexamic acid, niacinamide, arbutin, and Vitamin C. The composition comprises any combination of the active ingredients in the range from about 1.0% to about 6.0% by weight. In one embodiment, the composition comprises tranexamic acid in the range from about 1.0% to about 5.0% by weight, preferably 3.0%. In one embodiment, the composition comprises niacinamide in the range of about 3.0% to about 5.0% by weight. In one embodiment, the composition comprises arbutin about 3.0% percent by weight. In one embodiment, the composition comprises Vitamin C in the range from about 2.0% to about 5.0% by weight. In one embodiment, Vitamin C is Tetrahexyldecyl Ascorbate. In one embodiment, the Tetrahexyldecyl Ascorbate is an oil soluble.

The composition further comprises water, caprylic/capric triglyceride, C12-15 Alkyl Benzoate, Isononyl Isononanoate, Silica, Glyceryl Stearate, and PEG-100 Stearate, Cetearyl Alcohol and Ceteareth-20, Xylitylglucoside and Anhydroxylitol and Xylitol, Hydroxyethyl Acrylate/Sodium Acryloyldimethyl Taurate Copolymer, Polysorbate 60, Phenoxyethanol and Ethylhexylglycerin, Citric Acid, Titanium Dioxide, Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil, sh-Polypeptide-22, and sh-Oligopeptide-1.

In one embodiment, the method 100 for preparing the medicinal and cosmetic composition comprises the following steps. At step 102, phase-A is prepared by dissolving Titanium dioxide into water under moderate mixing. At step 104, Hydroxyethyl Acrylate/Sodium Acryloyldimethyl Taurate Copolymer is added to phase-A and the mixture is heated until fully hydrated. In one embodiment, the mixture is heated to about 80° C. At step 106, phase-B is prepared by heating and mixing one or more ingredients including Caprylic/Capric Triglyceride, Isononyl Isononanoate, C12-15 Alkyl Benzoate, Glyceryl Stearate and PEG-100 Stearate, Cetearyl Alcohol and Ceteareth-20, Tetrahexyldecyl Ascorbate, and Polysorbate 60. The ingredients are weigh-in and heated in a separate container. In one embodiment, the mixture is heated to about 80° C. with moderate mixing.

At step 108, main phase is prepared by adding phase-B to phase-A. In one embodiment, phase-B is slowly added to phase-A at about 80° C. and continuously mixed for about 5 minutes. Then the heat is turned off. At step 110, one or more ingredients such as Phenoxyethanol and Ethylhexylglycerin, Tranexamic Acid, Niacinamide, and Arbutin are added to the main phase. The ingredients are continuously mixed until all solids dissolved. At step 112, silica is added to the mixer obtained at step 110. At step 114, further ingredients such as Xylitylglucoside and Anhydroxylitol and Xylitol, Sh-Oligopeptide-1, Sh-Polypeptide-22, and Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil are added to the mixer obtained at step 112 and mixing until obtaining homogeneous. In one embodiment, the further ingredients are added to the mixer of previous step at about 40° C. and mixed continuously until homogeneous.

In one embodiment, the composition comprises two synthetic growth factors: Epidermal growth factor (EGF) and transforming growth factor-B1 (TGF-Beta 1). In one embodiment, the composition comprises EGF of about 10 ug/ml. In one embodiment, the composition comprises the TGF-Beta 1 in the range from about 10 ug/ml to about 20 ug/ml. In one embodiment, the composition has a pH of about 6.38 (as is at 25° C.). In one embodiment, the composition has a viscosity of about 183.000 cps (at 25° C., RVT spindle 63, and 5 rpm). In one embodiment, the composition is a serum, a lotion, a cream, a hydrogel, a mask, a stick, or a patch. In one embodiment, the composition is applied to an area of skin of the face, neck, hands having signs of aging, or on an area presenting wrinkles or skin lines. The composition reduces skin damage and provides toning to the skin.

Referring to Table 1, a list of ingredients, compounds and/or elements utilized for preparing the medicinal and cosmetic composition for treating hyperpigmentation, according to one embodiment of the present invention is disclosed as percent by weight, includes the International Nomenclature Cosmetic Ingredient (INCI) nomenclature:

TABLE 1

| TRADE NAME (example) | INCI NAME/ Ingredient | FUNCTION/ BENEFITS | Current wt. Percent | Minimum Range | Maximum Range |
| --- | --- | --- | --- | --- | --- |
| Water | Water | Solvent | 57.2470 | 30.0000 | 80.0000 |
| AE Ester CCT | Caprylic/Capric Triglyceride | Conditioning Agent | 5.0000 | 1.0000 | 15.0000 |
| Finsolv ® TN | C12-15 Alkyl Benzoate | Conditioning Agent | 5.0000 | 1.0000 | 15.0000 |
| AE Ester ® 99 | Isononyl Isononanoate | Conditioning Agent | 5.0000 | 1.0000 | 15.0000 |

TABLE 1-continued

| TRADE NAME (example) | INCI NAME/ Ingredient | FUNCTION/ BENEFITS | Current wt. Percent | Minimum Range | Maximum Range |
|---|---|---|---|---|---|
| Niacinamide PC | Niacinamide | Anti-aging Agent | 5.0000 | 0.1000 | 10.0000 |
| Arbutin | Arbutin | Brightening Agent | 3.0000 | 0.1000 | 5.0000 |
| Tranexamic Acid | Tranexamic Acid | Brightening Agent | 3.0000 | 0.1000 | 5.0000 |
| Silisphere ™6M | Silica | Rheology Modifier | 3.0000 | 0.5000 | 15.0000 |
| Lipomulse ®165 | Glyceryl Stearate and PEG-100 Stearate | Emulsifier | 3.0000 | 0.5000 | 10.0000 |
| Lipowax ™ D | Cetearyl Alcohol and Ceteareth-20 | Emulsifier | 3.0000 | 0.5000 | 10.0000 |
| BV-OSC | Tetrahexyldecyl Ascorbate (Vitamin C) | Brightening Agent | 2.0000 | 0.1000 | 10.0000 |
| Aquaxyl ™ | Xylitylglucoside and Anhydroxylitol and Xylitol | Moisturizer | 2.0000 | 0.1000 | 10.0000 |
| Sepinov ® EMT-10 | Hydroxyethyl Acrylate/Sodium Acryloyldimethyl Taurate Copolymer | Thickener/Emulsifier | 1.0000 | 0.1000 | 5.0000 |
| Liposorb ™ S-20 | Polysorbate 60 | Emulsifier | 1.0000 | 0.1000 | 5.0000 |
| AE Protek ® Plus | Phenoxyethanol and Ethylhexylglycerin | Preservative | 1.0000 | 0.1000 | 1.2000 |
| Citric Acid | Citric Acid | pH Adjuster | 0.4000 | 0.3000 | 0.5000 |
| TiO2 3328 | Titanium Dioxide | Colorant | 0.3000 | 0.1000 | 3.0000 |
| Citrus Oil Blend C105724 | Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil | Fragrance | 0.0500 | 0.0100 | 2.0000 |
| TGF-β1 | Sh-Polypeptide-22 | Anti-aging Agent | 0.0020 | 0.0001 | 1.0000 |
| EGF | Sh-Oligopeptide-1 | Anti-aging Agent | 0.0010 | 0.0001 | 1.0000 |
| | | | 100.0000 | | |

In embodiments, caprylic triglyceride is usually made from combining coconut oil with glycerin and works as a smoothing agent and an antioxidant.

In embodiments, C12-15 Alkyl Benzoate Versatile is an emollient ester suitable and improve feel, softness whilst offering and many other textural aspects whilst offering excellent emolliency with added pigment-dispersing capabilities.

In embodiments, Isononyl isononanoate is synthetic ester that functions as an emollient skin-softening agent that may naturally in cocoa oil and lavender oil.

In embodiments, niacinamide is a form of Vitamin B-3, an essential nutrient and can help build proteins in the skin and lock in moisture to prevent environmental damage and operates as an anti-aging agent.

In embodiments, arbutin is a glycoside, or a glycosylated hydroquinone extracted from the bearberry plant in the genus Arctostaphylos among many other medicinal plants, primarily in the family Ericacea and inhibits tyrosinase and thus prevents the formation of melanin.

In embodiments, tranexamic acid is in a class of medications called antifibrinolytics used to treat bleeding and works to improve blood clotting.

In embodiments, silisphere 6M is comprised of porous silica microbeads and is a smooth and silky material and as a rheology modifier.

In embodiments, lipomulse 165 is a pre-blend emulsifier system for all oil-in-water emulsions that stabilizes hydrogen peroxide formulations and acid pH products.

In embodiments, lipowax D is a high molecular weight saturated fatty alcohols and their ethylene oxide adducts in ratios and is used as an emulsifier system In embodiments, BV-OSC is a topical Vitamin C that is an oil soluble. With oil soluble Vitamin C, a higher percentage of Vitamin C is not needed due to the deeper level of skin penetration that the oil soluble solution provides.

In embodiments, aquaxyl is a blend of three ingredients that are plant derived, xylitylglucoside, anhydroxylitol, and xylitol. These ingredients target dry and dehydrated skin as such, aquaxy improves water circulation.

In embodiments, sepinov EMT-10 is thickening, stabilizing powder polymer.

In embodiments, liposorb S-20 is an oil-in-water emulsifier which adds water dispersibility to anhydrous systems.

Phenoxyethanol and Ethylhexylglycerin acts a preservative. In embodiments, citric acid is the starting point of the tricarboxylic acid cycle. Citric acid is traditionally produced from *Aspergillus*. Citric acid is an organic carboxylic acid and can be extracted from the juice of citrus fruits. Citric acid is used in the food and beverage industry for various purposes.

In embodiments, TiO2 3328 also known as titanium dioxide and is non-toxic and is used as a colorant for creams, lotions, powders, eye shadows, lipsticks and other cosmetics.

In embodiments, Citrus Oil Blend CI05724 comprises Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil for scent/fragrance.

In embodiments, TGF-β1 also known as transforming growth factor beta 1 is a polypeptide member of the transforming growth factor beta superfamily of cytokines.

In embodiments, EGF is known as epidermal growth factor and it reduces and prevents lines and wrinkles by generating new skin cells. Its properties allow for skin to be regenerated and helps with the removal of scars and blemishes.

In another embodiment, the composition comprises 3.0 to 10.0 wt. % Caprylic/Capric Triglyceride, 3.0 to 10.0 wt. % C12-15 Alkyl Benzoate, 3.0 to 10.0 wt. % Isononyl Isononanoate, 3.0 to 7.0 wt % Niacinamide, 2.0 to 4.0 wt. % Arbutin, 2.0 to 4.0 wt. % Tranexamic Acid, 2.5 to 10.0 wt. % Silica, 3.0 to 8.0 wt. % Glyceryl Stearate and PEG-100 Stearate, 3.0 to 8.0 wt. % Cetearyl Alcohol and Ceteareth-20, 3.0 to 8.0 wt. % Tetrahexyldecyl Ascorbate, 3.0 to 8.0 wt. % Xylitylglucoside and Anhydroxylitol and Xylitol, 2.0 to 4.0 wt. % Hydroxyethyl Acrylate/Sodium Acryloyldimethyl Taurate Copolymer, 0.05 to 3.0 wt. % Polysorbate 60, 0.5 to 1.0 wt. % Phenoxyethanol and Ethylhexylglycerin, 0.35 to 0.45 Citric Acid, 0.2 to 1.0 wt. % Titanium Dioxide, 0.05 to 1.5 wt. % Citrus Aurantium Bergamia (Bergamot) Fruit Oil and Citrus, 0.2 to 1.5 wt. % Grandis (Grapefruit) Peel Oil and Citrus Aurantium Dulcis, 0.001 to 0.07 wt. % Sh-Polypeptide-22, 0.001 to 0.07 wt. % sh-Oligopeptide-1, the remainder water.

EXAMPLES

The following examples are included to demonstrate preferred embodiments of the invention. It should be appreciated by those of skill in the art that the techniques disclosed in the examples which follow represent techniques disclosed by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Table 1 presents the formulation and the list of components of the composition. The table comprises one or more anti-aging agents, conditioning agents, brightening agents, and emulsifiers. In one embodiment, the anti-aging agents are niacinamide (Niacinamide PC), Sh-Polypeptide-22 (TGF-01), and Sh-Oligopeptide-1 (EGF). In one embodiment, the conditioning agents are caprylic/capric triglyceride (AE Ester CCT), C12-15 Alkyl Benzoate (Finsolv TN), and Isononyl Isononanoate (AE Ester 99). In one embodiment, the brightening agents are arbutin, tranexamic acid, and Tetrahexyldecyl Ascorbate (BV-OSC). In one embodiment, the emulsifiers are Glyceryl Stearate and PEG-100 Stearate (Lipomulse 165), Cetearyl Alcohol and Ceteareth-20 (Lipowax D), and Polysorbate 60 (Liposorb S-20).

In one embodiment, the composition further comprises water as solvent and silica (Silisphere 6M) as rheology modifier. In one embodiment, the composition further comprises Xylitylglucoside and Anhydroxylitol and Xylitol (Aquaxyl™) as moisturizer. In one embodiment, the composition further comprises Hydroxyethyl Acrylate/Sodium Acryloyldimethyl Taurate Copolymer (Sepinov™ EMT-10) as thicker/emulsifier. In one embodiment, the composition further comprises Phenoxyethanol and Ethylhexylglycerin (AE Protect Plus) as preservative. In one embodiment, the composition further comprises Titanium Dioxide (TiO2 3328) as colorant. In one embodiment, the composition further comprises citric acid as pH adjuster. In one embodiment, the composition further comprises fragrance comprising Citrus Aurantium Bergamia (Bergamot) Fruit Oil and Citrus Grandis (Grapefruit) Peel Oil and Citrus Aurantium Dulcis (Orange) Peel Oil and Citrus Tangerina (Tangerine) Peel Oil (Citrus Oil Blend CI05724).

Example 1

Methods:

A single-center, prospective, randomized, controlled split-face study has investigated the safety and efficacy of the composition compared to HQ4% in treating hyperpigmentation. Participants over the age of 18 with facial pigmentation are randomly assigned to have one side of their face treated with the composition twice a day (morning and night application) and the other treated with HQ4% applied at night. Patients or participants or subjects use a 5-point scale to self-assess their overall appearance, and a 4-point scale to assess the redness, irritation, and tolerability to the skin brightening creams. A Wilcoxon Signed Rank Test is used to test whether there is a statistical difference between the two treatments.

The composition-treated hyperpigmentation has a statistically significant improvement in the overall appearance of hyperpigmentation and is shown to be 28.5% better than HQ4%-treated skin in the patient self-assessment, and 27.0% better than HQ4%-treated skin in the independent reviewer assessment. On pair-wise comparison, the independent reviewer assessment also shows that 88.2% of the composition-treated sides appeared equal or better than the HQ4%-treated sides. No patients experienced intolerance to the composition, and all are able to continue its use without adverse effects. The composition treated hyperpigmentation also has a statistically significant reduction in irritation when compared to HQ4%-treated hyperpigmentation. Patients reported a reduction in redness when using the composition as opposed to HQ4%, but these figures did not reach statistical significance.

The composition significantly improves the appearance of hyperpigmentation when compared to HQ4% in both patient self-assessment and independent reviewer assessment. The composition exhibits a lower adverse reaction profile and is significantly better tolerated than HQ4%. Therefore, the composition could be considered as a safe and effective non-HQ alternative for the management of hyperpigmentation.

Various growth factors such as epidermal growth factor (EGF), tumor necrosis factor alpha 5(TNFα), interleukins 1 and 6 (IL-1, IL-6), Dickkopf 1 (DKK1), and transforming growth factor (TGF-β1) may be used herein. The composition comprises synthetic recombinant human epidermal growth factor (EGF) and tranexamic acid as the key ingredients in the topical formulation. Both EGF and tranexamic acid are implicated in improving hyperpigmentation. The composition also comprises other synthetic recombinant human growth factors along with Vitamin C, arbutin and niacinamide, all of which have been individually shown to improve hyperpigmentation). In this perspective, randomized, split study, the efficacy and safety of the composition are evaluated and compared to hydroquinone 4.0% (HQ4%).

Example 2

Study Design and Population:

This single-center, prospective, randomized, controlled study investigates the safety and efficacy of the proprietary product the composition compared to HQ4% in treating hyperpigmentation.

Hydroquinone 4.0% (HQ4%) is mixed in a pre-manufactured anhydrous topical gel consisting of the following inactive ingredients: dimethicone, caprylyl methicone, PEG-12 dimethicone/PPG-20 crosspolymer, butyrospermum parki (shea) butter, polysilicone-11, tocopheryl acetate, and BHT (PCCA WO6 Anhydrous Topical Gel, Houston, Tex., USA). Tocopheryl acetate and BHT are not active ingredients and are serving as preservatives in this formula.

The active ingredients are mixed in a moisturizing cream base consisting of the inactive ingredients. The inactive ingredients are water, caprylic/capric triglyceride, isononyl isononanoate, C12-15 alkyl benzoate, silica, cetearyl alcohol, glyceryl stearate, PEG-100 stearate, ceteareth-20, polysorbate 60, hydroxyethyl acrylate/sodium acryloyldimethyl taurate copolymer, xylitylglucoside, anhydroxylitol, xylitol, phenoxyethanol, ethylhexylglycerin, titanium dioxide, citric acid, citrus aurantium bergamia (bergamot) fruit oil, citrus grandis (grapefruit) peel oil, citrus aurantium dulcis (orange) peel oil, and citrus tangerina (Tangerine) peel oil.

Participants over the age of 18 with the pigmentation of the face, as determined by clinical examination, are included in this study. Subtypes of hyperpigmentation that met inclusion criteria are melasma, post-inflammatory hyperpigmentation, and/or solar lentigines. Each patient is required to be free of using any whitening creams, retinol-based products, or treatments to correct their hyperpigmentation (i.e. lasers, peels) for the past 6 months. Additionally, patients are required to be out of the direct sun during the duration of the treatment. Female patients who are pregnant, planning to be pregnant or breast-feeding are also excluded from the study. Written informed consent is obtained from all study subjects before enrollment. The protocol for the study is conducted according to the Declaration of Helsinki and the Health Insurance Portability and Accountability Act.

In this split study, participants are assigned based on a computer-generated randomization protocol such that one side of the face with hyperpigmentation is treated with the composition twice a day (morning and night application) and the other side is treated with HQ4% applied night only. The early experience using the composition before the onset of this study shows that it is well tolerated for use twice daily, while HQ4% is better tolerated at night. All patients are instructed to apply a zinc-oxide based sunscreen to both sides of the face with SPF 30 that is provided to them.

Assessments:

The study assesses hyperpigmentation at baseline (before treatment) and at one month after treatment initiation using both patient self-assessment and independent reviewer assessments. Patients use a 5-point scale to self-assess their overall appearance; in each case a higher score denoted a better outcome. Patients also use a 4-point scale to assess the redness, irritation, and tolerability to the skin brightening compositions as presented in Table 1, which shows the self-assessment survey scale. For the patient self-assessment, a Wilcoxon Signed Rank Test is used to test whether there is a statistical difference between the two treatments in overall appearance, irritation, redness, and tolerability.

TABLE 2

Patient Self-Assessment Survey Scale

| Score | −1 | 0 | 1 | 2 | 3 |
|---|---|---|---|---|---|
| Overall appearance | Worsened | No change | Mild improvement | Moderate improvement | Significant improvement |
| Irritation | | None | Mild irritation | Moderate irritation | Significant irritation |
| Redness | | None | Mild redness | Moderate redness | Significant redness |
| Tolerability | | No issues | Mild issues | Moderate issues | Significant intolerability |

Three-dimensional imaging is performed before treatment is administered and again 1 month following treatment initiation using a standardized Canfield Vectra 3D imaging system (Canfield Scientific Inc., Parsippany, N.J.). The study utilizes five independent reviewers comprised of two dermatologists, two facial plastic surgeons, and one oculoplastic surgeon. Each reviewer is blinded to the study treatment, assessed the pre-treatment and post-treatment images, and graded the appearance of each side on overall appearance. The grading scale is as follows: −1 indicating worsened appearance, 0 indicating no change, 1 indicating mild improvement, 2 indicating moderate improvement, and 3 indicating significant improvement as presented in Table 2, which shows the independent reviewer assessment scale.

TABLE 3

Independent Reviewer Assessment Scale

| Score | −1 | 0 | 1 | 2 | 3 |
|---|---|---|---|---|---|
| Overall appearance | Worsened | No change | Mild improvement | Moderate improvement | Significant improvement |

Additionally, the independent reviewers also performed a qualitative comparative assessment of the sides treated with each cream and noted the "better overall" side. A Wilcoxon Signed Rank Test is used to test whether there is a statistical difference in overall appearance between the composition- and HQ4%-treated sides.

Results:

There are 18 patients including 16 females and 2 males who meet the inclusion criteria and are enrolled in the study.

The mean age of the patients is 38.8 (+/−9.7) years ranging from about 23 to about 61 years.

Example 3

Patient Self-Assessment:

After one month of treatment, the patients have assessed the two products from baseline on overall appearance, irritation, redness, and tolerability using a Likert scale as shown in Table 2. One patient dropped out of the study after two weeks due to severe irritation, redness, and intolerability from HQ4% use. This patient's last observation for HQ4% is carried forward to the one-month assessment.

Figure 2:
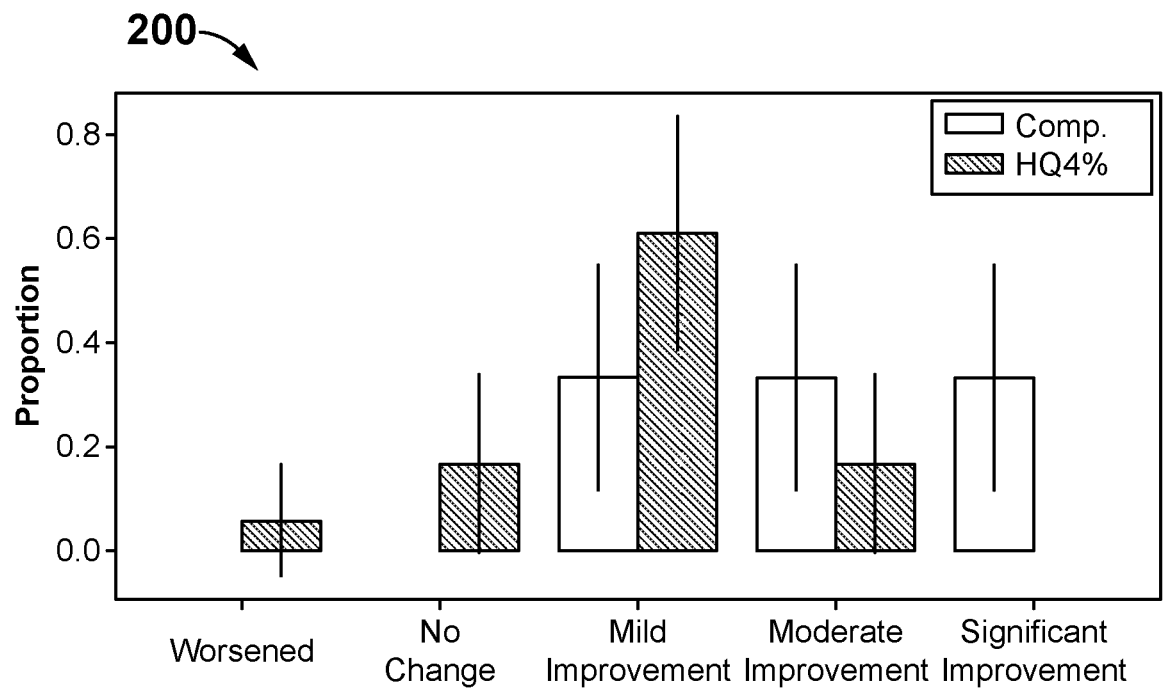
FIG. 2 shows a graph for patient self-assessment containing the distribution of overall appearance scores in one embodiment of the present invention.
Figure 3:
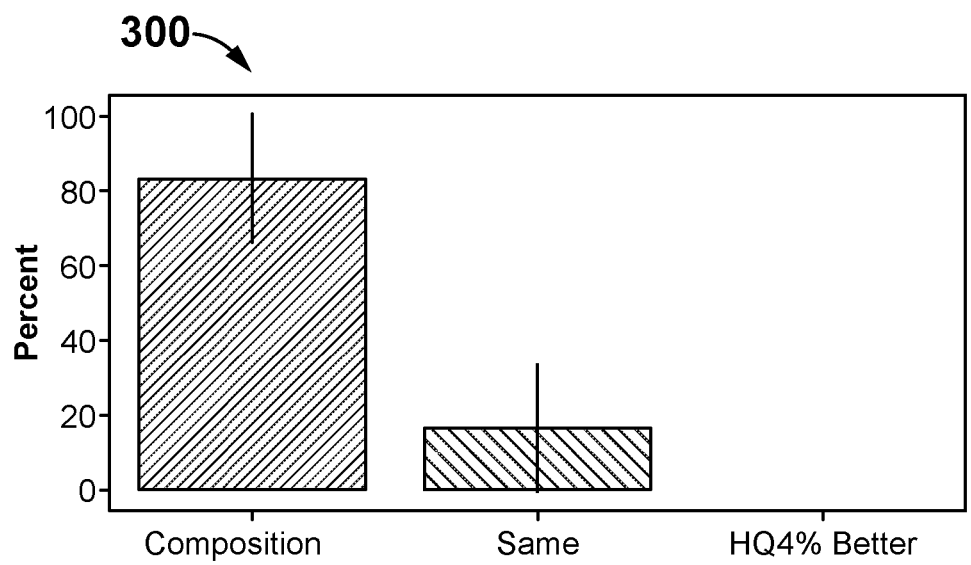
FIG. 3 shows a graph for patient self-assessment demonstrating the proportion of overall appearance scores of the composition and HQ4% in one embodiment of the present invention.

After one month of the composition treatment, 6 out of 18 (33.3%) have found a mild improvement, 6 out of 18 (33.3%) have found a moderate improvement, and 6 out of 18 (33.3%) have found a significant improvement in the overall appearance of their hyperpigmentation relative to baseline. After one month of HQ4% treatment, 1 out of 18 (5.6%) have found a worsening in overall appearance, 3 out of 18 (16.7%) have found no change, 11 out of 18 (61.1%) have found a mild improvement, and 3 out of 18 (16.7%) have found a moderate improvement in their hyperpigmentation relative to baseline, which are presented in a graph 200 shown in FIG. 2 a better overall appearance than the HQ4%-treated side. Out of 18 patients, 3 (16.7%, 0:0.0-33.9%) rate both the composition and HQ4%-treated sides as having the same overall appearance. None of the patients have rated the HQ4%-treated side as having a better overall appearance. The overall appearance scores of the composition and HQ4% are presented in a graph 300 shown in FIG. 3. Differences in pair-wise scores are statistically significant (p=0.001). After one month of treatment, patients report a 1000 improvement (mild, moderate, or significant) in overall appearance of the composition-treated skin sections and 77.8 improvement in HQ4%-treated skin sections. Relative to HQ4%, this is a 28.5% improvement with the composition.

TABLE 4

Patient self-assessment: Distribution of Overall Appearance Scores Irritation:

| Treatment | Score | Proportion (%) N = 18 Patients | 95% Margin of Error |
| --- | --- | --- | --- |
| The composition | Worsened | 0 (0.0%) | ±0.0% |
| | No Change | 0 (0.0%) | ±0.0% |
| | Mild Improvement | 6 (33.3%) | ±21.8% |
| | Moderate Improvement | 6 (33.3%) | ±21.8% |
| | Significant Improvement | 6 (33.3%) | ±21.8% |
| HQ4 % | Worsened | 1 (5.6%) | ±10.6% |
| | No Change | 3 (16.7%) | ±17.2% |
| | Mild Improvement | 11(61.1%) | ±22.5% |
| | Moderate Improvement | 3 (16.7%) | ±17.2% |
| | Significant Improvement | 0 (0.0%) | ±0.0% |

Figure 4:
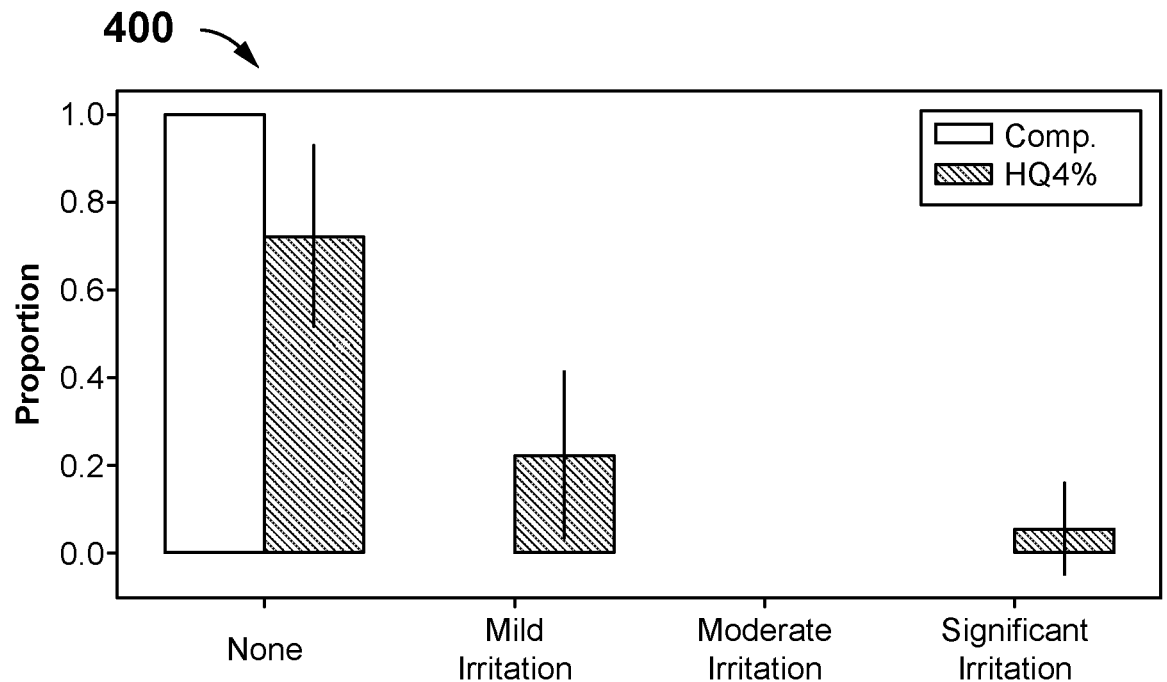
FIG. 4 shows a graph for patient self-assessment demonstrating the distribution of irritation scores in one embodiment of the present invention.

After one month, 100.0% of patients report no irritation on the composition-treated side. In contrast, 13 out of 18 (72.2%) patients report no irritation, 4 out of 18 (22.2%) reported mild irritation, and 1 out of 18 (5.6%) reports significant irritation on the HQ4%-treated side, which are presented in a graph 400 shown in FIG. 4. On pair-wise comparison, 5 out of 18 (27.8%, CI: 7.1-48.5%) patients report less irritation with the composition-treated side while none has reported less irritation with the HQ4%-treated side. Differences in pair-wise scores are mildly statistically significant (p=0.048).

Figure 5:
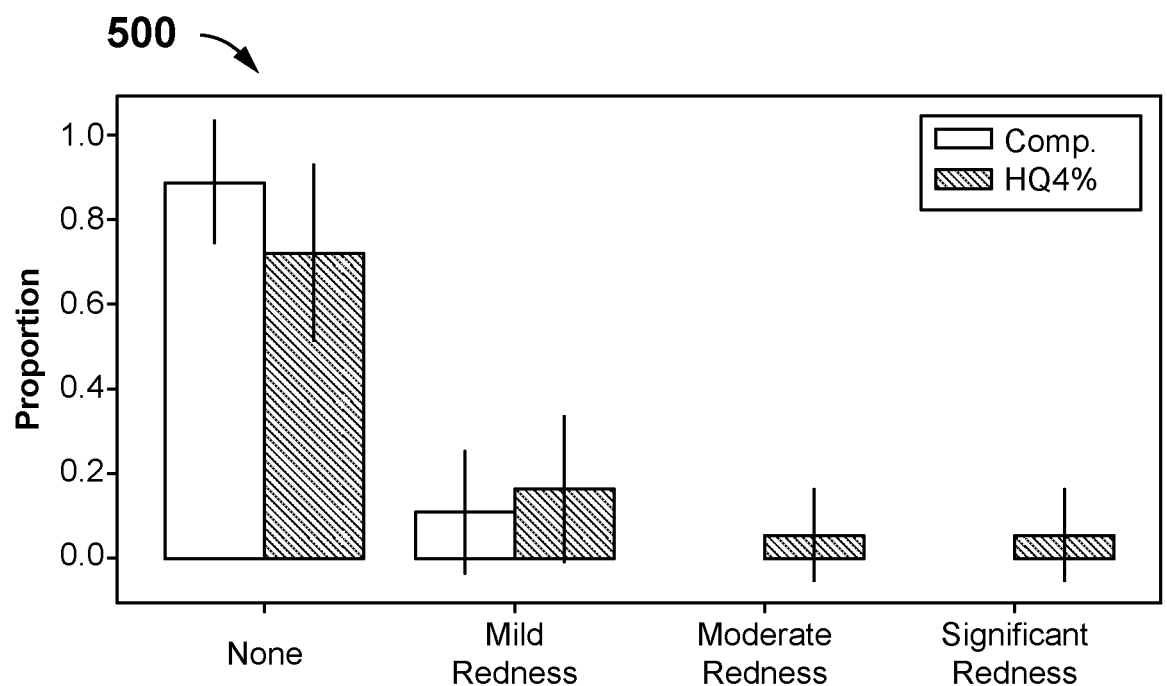
FIG. 5 shows a graph for patient self-assessment demonstrating the distribution of redness scores in one embodiment of the present invention.

Redness:

After one month, 16 out of 18 (88.9%) patients report no redness and 2 out of 18 (11.1%) report mild, transient redness on the composition-treated side while 13 out of 18 (72.2%) patients report no redness, 3 out of 18 (16.7%) reported mild redness, 1 out of 18 (5.6%) report moderate redness, and 1 out of 18 (5.6%) reports significant redness on the HQ4%-treated side, which are presented in a graph 500 shown in FIG. 5. On pair-wise comparison, 5 out of 18 (27.8%, CI: 7.1-48.5%) of patients report less redness with the composition-treated side, while 2 out of 18 patients (11.1%, CI: 0.0-25.6%) report less redness with the HQ4%-treated side. Differences in pair-wise scores did not reach statistical significance (p=0.19).

Figure 6:
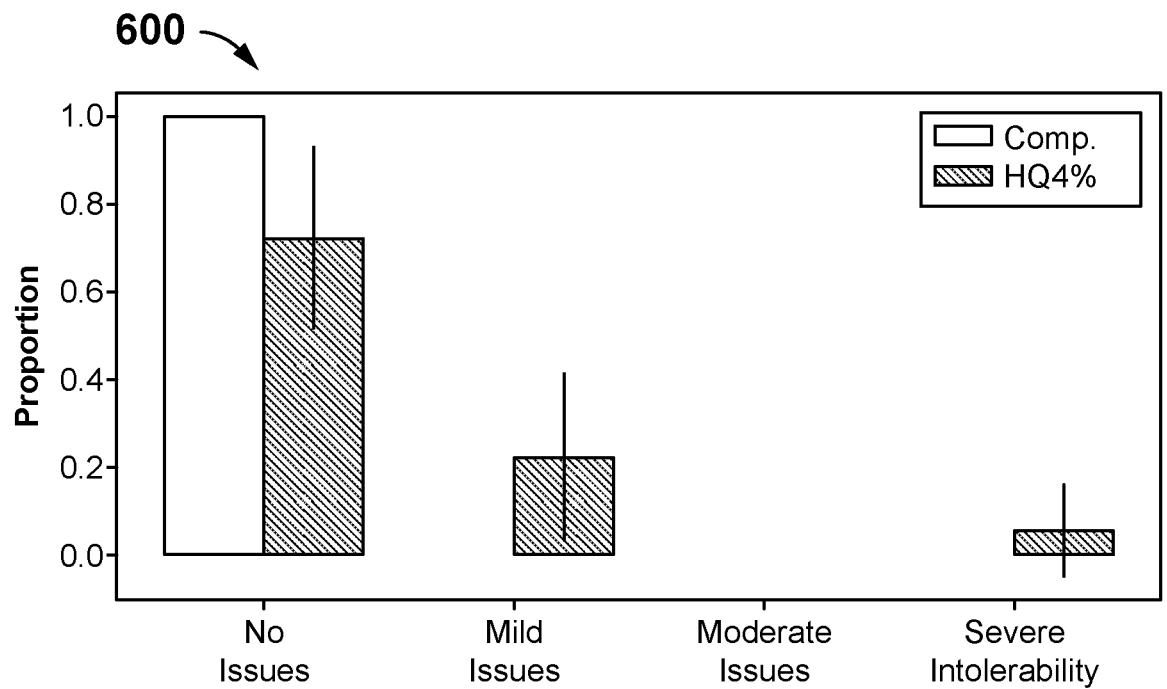
FIG. 6 shows a graph for patient self-assessment demonstrating the distribution of tolerability scores in one embodiment of the present invention.

Tolerability:

After one month of the composition treatment, 100.0% of patients report no tolerability issues. After one month of HQ4%, 13 out of 18 (72.2%) patients report no tolerability issues, 4 out of 18 (22.2%) report mild tolerability issues and 1 out of 18 (5.6%) reports severe intolerability, which are present in a graph 600 shown in FIG. 6. On pair-wise comparison, 5 out of 18 (27.8%, CI: 7.1-48.5%) patients report better tolerability to treatment with the composition-treated side compared to the HQ4%-treated side while none has reported better tolerability to treatment with the HQ4%-treated side. Differences in pairwise scores are mildly statistically significant (p=0.048).

Example 4

Figure 7:
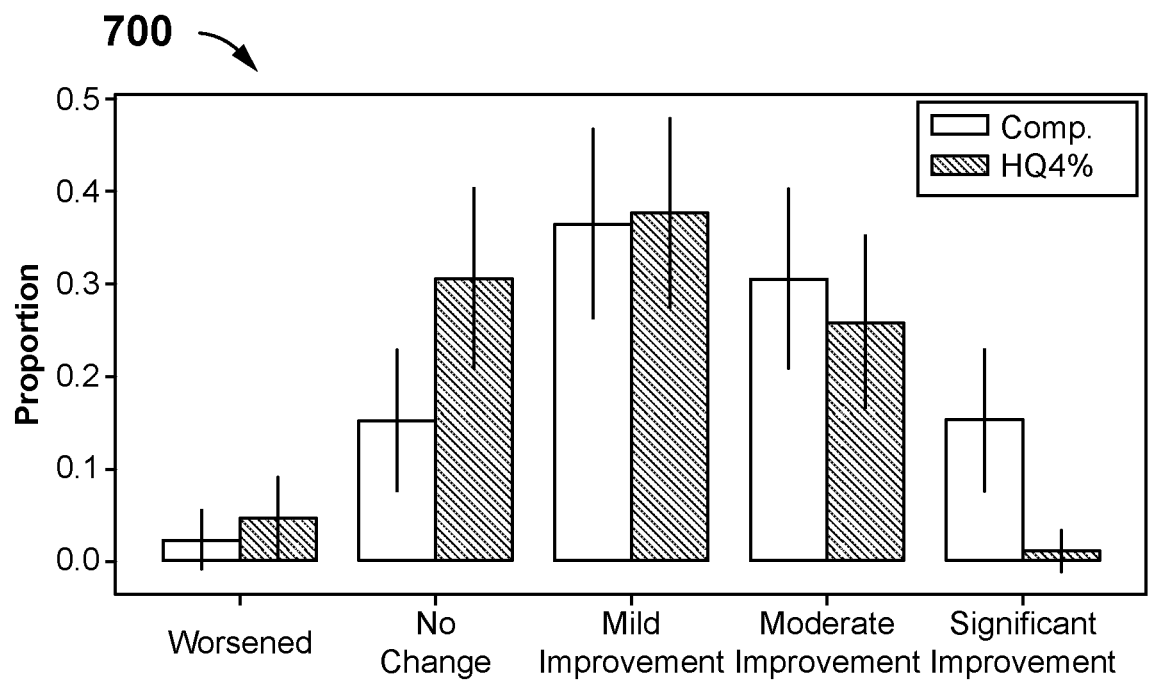
FIG. 7 shows a graph for independent reviewer assessment demonstrating distribution of scores in one embodiment of the present invention.

Independent Reviewer Assessment:

There are 17 patients including 15 females and 2 males in the Independent Reviewer Assessment. The mean age of the patients is 39.7+/−9.1 (range: 27 to 61 years). One patient dropped out of the study due to intolerability to HQ4%. Five independent evaluators have reviewed 17 patients, for a total of 85 ratings that are taken into analysis. After one month of treatment, evaluators reported an improvement (whether mild, moderate, or significant) in overall appearance in 70 out of 85 cases (82.4%) on the composition-treated side and in 55 out of 85 cases (64.7%) on the HQ4%-treated side, which are presented in a graph 700 shown in FIG. 7 and Table 5. Relative to HQ4%, this is a 27.0% improvement.

TABLE 5

Independent Reviewer Assessment: Distribution of Evaluator Scores for Overall Appearance

| Treatment | Score | Score Counts (%) N-85 | 95% Margin of Error |
| --- | --- | --- | --- |
| The composition | Worsened | 2 (2.4%) | ±3.2% |
| | No Change | 13 (15.3%) | ±7.7% |
| | Mild Improvement | 31 (36.5%) | ±10.2% |
| | Moderate Improvement | 26 (30.6%) | ±9.8% |
| | Significant Improvement | 13 (15.3%) | ±7.7% |
| HQ4 % | Worsened | 4 (4.7%) | ±4.5% |
| | No Change | 26 (30.6%) | ±9.8% |
| | Mild Improvement | 32 (37.6%) | ±10.3% |
| | Moderate Improvement | 22 (25.9%) | ±9.3% |
| | Significant Improvement | 1 (1.2%) | ±2.3% |

Figure 8:
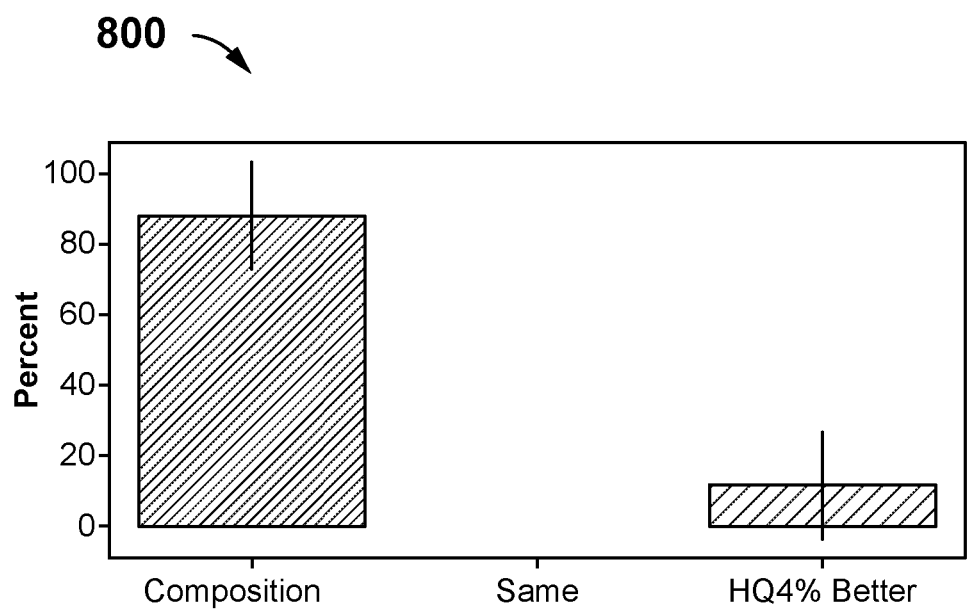
FIG. 8 shows a graph for independent evaluator assessment demonstrating the proportion of evaluator scores for which the composition is better, same, or worse than HQ4% in one embodiment of the present invention.

On pair-wise comparison, 31 out of 85 (36.5%, CL: 26.3-46.7%) of the composition-treated cases are rated as being equal in overall appearance by the independent evaluators to the HQ4%-treated cases. 44 out of 85 (51.8%, CIL 41.2-62.4%) of the composition-treated cases are rated as having better overall appearance by the independent evaluators than the HQ4%-treated cases. Out of 85 HQ4%-treated cases, 10 (11.8%, CIL 5.0-18.6%) are rated as having a better overall appearance, which are presented in a graph 800 shown in FIG. 8 and Table 6 than the composition-treated cases. In summary, on pair-wise comparison, the independent reviewer assessment shows that evaluators gave higher scores to the composition-treated sides compared to HQ4%-treated sides (p<0.001). Most notably, 88.2% of the composition-treated sides appears equal or better than the HQ4%-treated sides.

TABLE 6

Independent Reviewer Assessment: Proportion of evaluator scores for which the composition is better, same, or worse than HQ4 %

| Side | Proportion (%) | 95% Margin of Error |
| --- | --- | --- |
| The composition better | 44/85 (51.8%) | ±10.6% |
| Same | 31/85 (36.5%) | ±10.2% |
| HQ4 % better | 10/85 (11.8%) | ±6.8% |

Example 5

Outcomes:

Hyperpigmentation is a dermatologic condition that causes unappealing appearance in a variety of individuals. The current mainstay of treatment is topical hydroquinone (HQ), which is available in over-the-counter 2.0% and prescription 4.0% formulations. Despite possessing excellent skin-lightening properties, HQ's usage remains controversial, and studies suggest potentially carcinogenic and toxic effects affecting a variety of tissues. Therefore, this study aims to determine if the use of a potential non-HQ alternative formulation provides equal or greater efficacy with a reduced adverse reaction profile.

In this study, patients who are suffering from hyperpigmentation treated with the composition have a statistically significant improvement in the overall appearance of hyperpigmentation and shown to be 28.5% better than HQ4%-treated skin based on mild to significant improvement ratings. The composition-treated patients also have a statistically significant reduction in irritation when compared to HQ4%-treated patients with hyperpigmentation. Though patients are reported a reduction in redness when using the composition as opposed to HQ4%, these figures did not reach statistical significance. One patient experienced severe intolerance to HQ, and unable to continue the full duration of the treatment. No patients experienced intolerance to the composition, and all could continue its use without adverse effects.

Given the potential difficulty in evaluating the clinical differences and changes in hyperpigmentation within the patient's baseline and one-month images, 5 independent physicians are recruited to evaluate and treat hyperpigmentation in their daily practice to assess the before and after treatment images. The results show that the assessments are very similar between the five reviewers with a strong inter-reliability. The reviewers' pair-wise comparison data shows that 88.2% of the composition-treated side appears either the same or better than the HQ4%-treated side. This study supports the composition as an alternative, non-HQ product that could be used to improve skin hyperpigmentation, such as melasma, post-inflammatory hyperpigmentation, and solar lentigines.

The composition's ability to effectively improve hyperpigmentation could be attributed to its unique blend of ingredients that all have demonstrated safety and efficacy from prior peer reviewed medical journal publications, which is described in more detail below. Tranexamic acid (TA) has emerged as an effective treatment for hyperpigmentation including melasma. The mechanism of action for the reduction in hyperpigmentation is due to TA's ability to decrease tyrosinase activity in melanocytes. Topical TA formulations have been shown to be effective in the treatment of hyperpigmentation and melasma; 2.0% emulsion, 3.0% cream, 5.0% solution, and 5.0% liposomal cream have all been clinically studied. Topical TA applications demonstrate equal efficacy in reducing melasma when compared to HQ alone, topical HQ plus dexamethasone, and intradermal injections of TA.

The composition has increased efficacy in treating hyperpigmentation relative to the current standard treatment HQ4%. In addition to improving the appearance of hyperpigmentation as seen through both patient reported and independent reviewer assessments, the composition also demonstrated better tolerability, as well as reduced redness and irritation relative to HQ4%. Also, the composition has been found to be safe and effective for use in hyperpigmentation.

Preferred embodiments of this invention are described herein, including the best mode known to the inventors for carrying out the invention. It should be understood that the illustrated embodiments are exemplary only and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A composition to improve hyperpigmentation comprising 3.0 wt. % Tranexamic acid, 5.0 wt. % Niacinamide, 3.0 wt. % Arbutin, 2.0 wt. % Tetrahexyldecyl Ascorbate, 0.0001 wt. % sh-Oligopeptide-1, and 0.0002 wt. % sh-Polypeptide-22.

2. The composition of claim 1, wherein the composition further comprises 1.0 to 15.0 wt. % Capric Triglyceride, 1.00 to 15.00 wt. % C12-15 Alkyl Benzoate, 1.00 to 15.00 wt. % Isononyl Isononanoate, 1.00 to 15.00 wt. %, 0.50 to 15.0 wt. 00 Silica, 0.10 to 5.00 wt. % Polysorbate 60, 0.30 to 0.50 wt. % Citric Acid, 0.10 to 3.00 wt. % Titanium Dioxide, 0.01 to 2.00 wt. % Citrus Oil, and 30.00 to 80.00 wt. % water.

* * * * *